(12) United States Patent
Guo et al.

(10) Patent No.: US 8,394,431 B2
(45) Date of Patent: Mar. 12, 2013

(54) COMPOSITION OF EXTRACTS FROM PLANTS AND THE USE THEREOF IN PROPHYLAXIS OR TREATMENT OF METABOLISM DISORDER OF BLOOD LIPID

(76) Inventors: Jiao Guo, Guangzhou (CN); Weijian Bei, Guangzhou (CN)

( * ) Notice: Subject to any disclaimer, the term of this patent is extended or adjusted under 35 U.S.C. 154(b) by 0 days.

(21) Appl. No.: 13/062,599

(22) PCT Filed: Jun. 2, 2009

(86) PCT No.: PCT/CN2009/072098
§ 371 (c)(1),
(2), (4) Date: Mar. 7, 2011

(87) PCT Pub. No.: WO2010/025631
PCT Pub. Date: Mar. 11, 2010

(65) Prior Publication Data
US 2011/0165273 A1   Jul. 7, 2011

(30) Foreign Application Priority Data

Sep. 5, 2008   (CN) .......................... 2008 1 0198361

(51) Int. Cl.
*A61K 36/254* (2006.01)
*A61K 36/258* (2006.01)

(52) U.S. Cl. ...................................................... 424/728
(58) Field of Classification Search ........................ None
See application file for complete search history.

(56) References Cited

U.S. PATENT DOCUMENTS 5,698,199 A * 12/1997 Mori et al. ..................... 424/734
2002/0068704 A1* 6/2002 Ziegler ............................. 514/27
2005/0037094 A1* 2/2005 Yan et al. ....................... 424/728

FOREIGN PATENT DOCUMENTS

| CN | 1398630 A | * | 2/2003 |
| CN | 1628786 A |   | 6/2005 |
| JP | 55122715 A | * | 9/1980 |
| JP | 06248267 A | * | 9/1994 |
| KR | 2001037594 A | * | 5/2001 |
| KR | 2004094955 A | * | 11/2004 |
| WO | WO 2004032924 A1 | * | 4/2004 |
| WO | WO 2005041985 A1 | * | 5/2005 |

OTHER PUBLICATIONS

International Search Report, PCT/CN2009/072098, dated Sep. 10, 2009.

* cited by examiner

*Primary Examiner* — Amy L Clark
(74) *Attorney, Agent, or Firm* — Lerner, David, Littenberg, Krumholz & Mentlik, LLP

(57) ABSTRACT

A composition of extracts from plants which can be used for prophylaxis or treatment of metabolism disorder of blood lipid, includes the following ingredients in weight: 3-10 portions of oleanolic acid, 1-5 portions of salvianolic acid, 1-5 portions of danshensu, 1-3 portions of berberine, 1-5 portions of *panax notoginseng* saponins, 1-5 portions of polysaccharides of atracty-lodes macrocephala koidz, 1-3 portions of aucubin, 1-5 portions of total flavone in *cirsium japonicum*, 1-5 portions of finger citron polysaccharide, 1-5 portions of *panax notoginseng* polysaccharides and 1-5 portions of flavones. The use of such composition in manufacturing medicaments used for prophylaxis or treatment of diseases related to metabolism disorder of blood lipid, and the use of such composition in manufacturing health food used for adjuvant prophylaxis or treatment of diseases related to metabolism disorder of blood lipid. Such composition significantly improved the bioavailability, increased the effectiveness, stability, controllability, convenience and safety of medication.

4 Claims, 2 Drawing Sheets

Attached drawings of the invention

US 8,394,431 B2

COMPOSITION OF EXTRACTS FROM PLANTS AND THE USE THEREOF IN PROPHYLAXIS OR TREATMENT OF METABOLISM DISORDER OF BLOOD LIPID

CROSS REFERENCE TO RELATED APPLICATIONS

The present application is a national phase entry under 35 U.S.C. §371 of International Application No. PCT/CN2009/072098, filed Jun. 2, 2009, which claims priority from Chinese Patent Application No. 200810198361.6, filed Sep. 5, 2008, the disclosures of said applications are hereby incorporated herein by reference herein.

TECHNICAL FIELD

The present invention relates to a composition of extracts from plants and its use in prophylaxis or treatment of metabolism disorder of blood lipid, which belongs to the field of pharmaceutical technology.

BACKGROUND ART

"Compound Zhenzhu Tiaozhi" (FTZ) is a Chinese traditional medicine composition for the treatment of hyperlipidemia with the desired effect and total clinical effective rate of 91%. This prescription is composed of 8 herbs: *ligustrum japonium*, sojutsu var, bergamot, *eucommia, cirsium japonicum, salvia miltiorrhiza*, coptsir root, and *panax notoginseng*. In this prescription, *ligustrum japonium* is put in an important position as principal drug for nourishing liver and kidney; sojutsu var is used in concert with *Ligustrum japonium* for invigorating the spleen and supplementing qi, eliminating dampness and diuresis and eliminating phlegm and turbid, then the spleen and kidney could be both invigorated; *eucommia* has effect of enriching kidney-yang, and is used in concert with *ligustrum japonium* for both enriching kidney yin and yang and acts as coordination between water and fire with *ligustrum japonium*, which leads to more significant effects of tonifying the kidney without worry of greasy or aid of fire; bergamot has effects of discharging liver and regulating qi, eliminating dampness and phlegm and eliminating phlegm in the blood to regulate qi-activity, when used with sojutsu var, bergamot has more significant effects of regulating the flow of qi, dispelling phlegm and eliminating dampness. Bergamot, sojutsu var and *eucommia* are subordinate drugs. *Cirsium japonicum* has effect of cooling blood to remove toxin and stasis; *salvia miltiorrhiza* has effect of promoting blood circulation to remove stasis; *panax notoginseng* has effect of stopping blood to remove stasis; and coptsir root has effect of clearing away heat and toxic materials and drying the damp, and these four drugs are adjuvant drugs. When all drugs are combined, will leads the prescription having the effects of strengthening spleen and nourishing kidney, discharging liver and regulating qi, removing heat-phlegm and removing toxin and stasis. The cooperation of warm and cool and the simultaneous deployment of strengthening vital qi and eliminating pathogenic factor are confirmed in this prescription. This prescription has effect of strengthening with promotion and no greasiness, and eliminating pathogen without affect vital qi to solve the conditions of "deficiency", "stagnation", "phlegm", "stasis", and "toxin". This prescription "FTZ" has obtained Chinese national patent of invention, and the patent number is ZL200410051250.4.

Although FTZ has good effects of blood lipid regulation and anti-atherogenic ability and clinical efficacy, it is a Chinese traditional herbal medicine compound preparation prepared by Chinese herbal medicines. It is very complex in composition and the active ingredient is not clear and difficult to quantify. In actual application, the quality of the products is difficult to obtain effective control, which will ultimately affect the stability of the clinical efficacy of products, and the formulations of the pharmaceutical preparations can not be various with limited application range.

DISCLOSURE OF THE INVENTION

Technical Solution

An objective of the present invention is to provide a composition of extracts from plants, the component of which is easy to quantify and the quality of which is easy to control.

Another objective of the present invention is to provide the use of such composition in preparing the pharmaceutical medicaments.

Another objective of the present invention is to provide the use of such composition in preparing healthy foods.

In the present invention, the above objectives are achieved by the following technical solution:

A composition of extracts from plants which can be used for prophylaxis or treatment of metabolism disorder of blood lipid, includes the following ingredients in weight: 3-10 portions of oleanolic acid, 1-5 portions of salvianolic acid, 1-5 portions of danshensu, 1-3 portions of berberine, 1-5 portions of *panax notoginseng* saponins, 1-5 portions of polysaccharides of atracty-lodes macrocephala koidz, 1-3 portions of aucubin, 1-5 portions of total flavone in *cirsium japonicum*, 1-5 portions of finger citron polysaccharide, 1-5 portions of *panax notoginseng* polysaccharides, and 1-5 portions of flavones. The flavones is a mixture of kaempferol, quercetol and apigenin by any proportion.

The use of such composition in manufacturing medicaments used for prophylaxis or treatment of diseases related to metabolism disorder of blood lipid.

The medicaments in the above use may be granular formulation, tablets, capsules, powders, pills, elixir or other oral preparations.

The use of such composition in manufacturing health food used for adjuvant prophylaxis or treatment of diseases related to metabolism disorder of blood lipid.

Beneficial Effects

Compared with the existing technology, the present invention has the following beneficial effects:
(1) The composition of extracts from plants further expand the application range of the active ingredient group in the compound Fufang tiaozhi, which provides a new way for prevention or treatment of lipid metabolism-related diseases;
(2) The composition of extracts from plants further expand the application of the compound Fufang tiaozhi in the field of pharmaceutical preparations, which significantly improves the bioavailability of the active ingredients in the compound Fufang tiaozhi. The animal tests showed that the composition has significant lipid-lowering effect in experimental hyperlipidemia, which can lower the impact of cholesterol and improve the lipid metabolism with no significant side effects observed and increased safety of medications.
(3) The composition of extracts from plants can be prepared through chemical synthesis. Compared with the materials directly extracted from plant, the purity of the materials are greatly improved. Because it is in the form of compound, but not herbs, the quality of prepared pharmaceutical preparations could be stable and controlled. The impurities have been greatly decreased compared with herbs directly used in medicine. The effectiveness of the drugs is improved and make the medicine easy to take off.

DETAILED DESCRIPTION OF THE INVENTION

Figure 1:
FIG. 1 is the test results graph of the composition of extracts from plants in example 3 promoting the expression of L-O2 lipoprotein lipase of liver cells gene (LPL mRNA).

The composition of extracts from plants of the invention can be expressed as FTZEC.

Example 1

Total weight of 15 kg, 3.5 portions of oleanolic acid, 1.5 portions of salvianolic acid, 1.5 portions of danshensu, 1.5 portions of berberine, 1 portion of *panax notoginseng* saponins, 1.5 portions of polysaccharides of atracty-lodes macrocephala koidz, 1.5 portions of aucubin, 1 portion of total flavone in *cirsium japonicum,* 1.5 portions of finger citron polysaccharide, 1 portion of *panax notoginseng polysaccharides, and* 1.5 portions of flavones were taken and mixed evenly to obtain the composition of extracts from plants of the invention (referred to FTZEC).

Added 10 kg of starch and 10 kg of dextrin in the FTZEC, mixed evenly, then added 75% ethanol to pelletize, dried at 80° C., added appropriate amount of magnesium stearate to form tablets and film-coated to obtain approximately 500,000 FTZEC tablets (70 mg/tablet), each tablet containing 30 mg of FTZEC.

Example 2

Acute Toxicity Test and Long Term Toxicity Test (1) Acute toxicity in mice: Total 120 of 19~21 g NIH mice (half male and half female) were divided into 6 groups, 20 mice in each group, and administrated by gavage (p.o.) with five different doses of FTZEC, using normal saline (NS) as the negative control. The responses in mice were observed and the number of dead mice in each group was recorded. Using the linear regression software of Microsoft Excel, a straight line was drew according to the logarithmic dose and experience probability unit to calculate LD50. LD50 of mice administrated by gavage with FTZEC were 10.88~12.50 g/kg, respectively.

(2) Long-term toxicity in rats: Total 120 Wistar rats (half male and half female) were divided into 4 groups, 30 rats in each group, and administrated by gavage (p.o.) with 3.0 g/kg, 1.50 g/kg, and 0.75 g/kg of FTZEC, using normal saline (NS) as the negative control. After successive administration for 180 days, there was no abnormal response in hemogram, heart and lung, liver and kidney function and nervous system function, and no significant pathological change in vital organs such as heart, lung, spleen, stomach, brain and intestines.

Conclusion: The composition of extracts from plants is low toxicity and high safety.

Example 3

Drug Efficacy Test

To investigate the effects of the composition of extracts from plants on key enzyme gene expression and activity of lipid metabolism.
1.1 Methods
1.1.1 Effects on the Activity of L-O2 Lipoprotein Lipase of Liver Cells (LPL) and Hepatic Lipase (HL)

The L-O2 human normal liver cells were cultured in routine way, various concentrations of FTZCE were respectively added after cells fusion, continuously cultured the cells for a certain time followed by collecting cells to prepare cell homogenates. Using LPL/HL detection kit (Nanjing Jiancheng Biotechnology Research Institute), the LPL/HL activity was detected by colorimetric method to research the effects of various composition of extracts from plants conbination on LPL activity and compare the enzyme activity of hepatocyte LPL/HL under the action of different concentrations of FTZEC. The gene expressions of hepatocyte LPL/HL were determined by RT-PCR method to observe the affects of FTZEC on the hepatocyte LPL/HL gene expression.
1.1.2 Effect on Inhibiting HMGCoA Reductase Activity Test the effects of various FTZEC conbination in vitro experiment on inhibiting HMGCoA reductase activity and calculate the $IC_{50}$ of the composition of extracts from plants on inhibition of HMGCoA reductase and compare with pravastatin.
1.2 Statistical Methods: Data was Represented as Mean±Standard Deviation and the Significance Test was Confirmed by Variance Analysis Method.
1.3 Results
1.3.1 Effect on Hepatocyte LPL/HL After treatment by various doses of FTZEC and FTZ, the activities of hepatocyte LPL/HL were significantly increased ($P<0.01$) with dose-dependent, and the results were in Table 1, which showed that the FTZEC has significant function of increasing hepatocyte LPL/HL.

TABLE 1

Effects of different drugs on the activity of L-O2 hepatocyte LPL/HL Enzyme activity unit (g FFA/mL supernatant · h)

| Group | Concentration (μg/ml) | n | LPL activity | HL activity |
|---|---|---|---|---|
| Normal | 0 | 7 | 12.63 ± 0.67 | 5.16 ± 0.46 |
| FTZ | 10.0 | 7 | 14.65 ± 2.52* | 6.65 ± 1.32* |
| FTZ | 50.0 | 7 | 16.62 ± 3.05** | 7.32 ± 1.55** |
| FTZEC1 | 10.0 | 7 | 15.98 ± 3.12* | 7.08 ± 2.12* |
| FTZEC1 | 50.0 | 7 | 17.65 ± 3.02** | 7.85 ± 2.32** |
| FTZEC1 | 100.0 | 7 | 18.18 ± 3.51** | 8.08 ± 2.31** |
| FTZEC2 | 50.0 | 7 | 16.60 ± 2.22** | 7.69 ± 2.02** |
| FTZEC3 | 50.0 | 7 | 16.41 ± 3.15** | 7.61 ± 2.15** |
| Fenofibrate | 50.0 | 7 | 16.95 ± 3.02** | 7.75 ± 1.92** |

Figure 2:
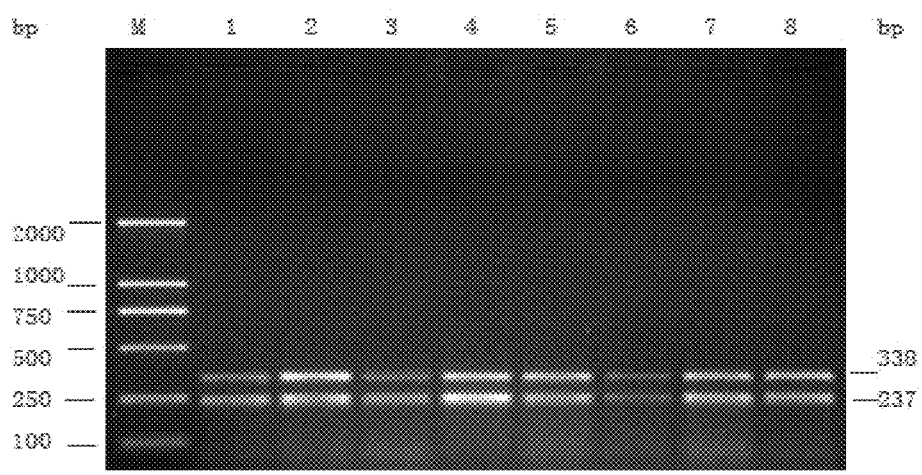
FIG. 2 is the test results graph of the composition of extracts from plants in example 3 promoting the expression of L-O2 hepatic lipase (HL mRNA) in human normal liver cells.

Note:
1) Compared with normal control group, *$P < 0.05$; **$P < 0.01$.
2) FTZ: extracts of Compound Zhenzhu tiaozhi In normal group, the gene expression of hepatocyte LPL was normal, the gene expression of hepatocyte LPL was significantly increased after treatment by different doses of FTZEC ($P<0.01$), which suggested that the FTZEC has obvious promotion on hepatic lipase gene expression ($P<0.01$), and the test results were shown in FIG. 1 and FIG. 2.

FIG. 1 showed that FTZEC has obvious promotion on L-O2 hepatocyte lipoprotein lipase. In FIG. 1, Lane 1 was Fenofibrate group; Lane 2 was the FTZ group; Lane 3 was the normal control group; Lane 4 was FTZEC low dose group; Lane 5 was FTZEC middle dose group; and Lane 6 was FTZEC high dose group.

FIG. 2 showed that FTZEC and FTZ have promotion on L-O2 hepatocyte hepatic lipase gene expression at different times. In FIG. 2, Lane 1 was the blank control for 3 hrs; Lane 2 was FTZEC group for 3 hrs; Lane 3 was blank control for 6 hrs; Lane 4 was FTZEC group for 6 hrs; Lane 5 was FTZ control for 6 hrs; Lane 6 was the blank control for 12 hrs; Lane 7 was FTZEC group for 12 hrs; and Lane 8 is FTZ control group for 12 hrs.

1.3.2 Inhibition on HMG-CoA Reductase Activity

The rats liver cells microsomes were prepared into HMG-CoA reductase solution. The activities of the HMG-CoA reductase were determined by literature method. The enzyme activity in each group was respectively determined to calculate the $IC_{50}$ (μg/ml) of FTZEC on HMG-CoA reductase activity.

Figure 3:
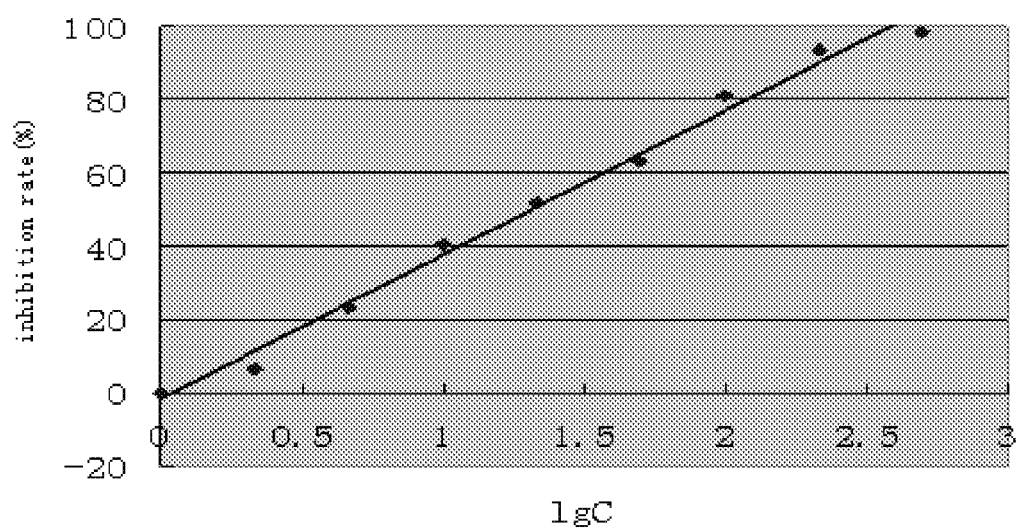
FIG. 3 is the test results graph of the composition of extracts from plants in example 3 inhibiting HMG-CoA reductase activity.

The results were shown in FIG. 3 and Table 2, which showed that FTZEC can significantly reduce activity of HMG-CoA reductase in a dose dependent manner. FTZEC can inhibit the activity of HMG-CoA reductase, hinder the synthesis of key material HMG-CoA in the synthesis of cholesterol, and inhibit the biosynthesis of cholesterol, resulting in reducing cholesterol.

TABLE 2

IC50 (μg/ml) of FTZEC on HMG-CoA reductase activity

| Drugs | $IC_{50}$ (μg/ml) |
| --- | --- |
| FTZEC1 | 1.35 ± 0.13 |
| FTZEC2 | 1.45 ± 0.15 |
| FTZEC3 | 1.12 ± 0.11 |
| FTZEC4 | 1.58 ± 0.13 |
| FTZEC5 | 1.75 ± 0.23 |
| Pravastatin | 1.85 ± 0.13 |
| FTZ | 3.85 ± 0.43 |

Example 4

To Investigate the Effects of FTZEC on Blood Lipid Metabolism of Dietary Hyperlipidemia in Experimental Animal Model 1. Experimental Materials
1.1 Drugs and Reagents
FTZEC: same as Experiment 1
FTZ: extracts from compound Zhenzhu tiaozhi
Total cholesterol, triglyceride, and high-density lipoprotein cholesterol assay kit.
1.2 Animals Clean SD rats, body weight (180-225 g), were provided by the experimental animal center of Southern Medical University.

Purebred New-Zealand female rabbits, body weight (1.80-2.20 kg), were provided by Guangdong Province Experimental Animal Center.
2. Experimental Methods
2.1 Effects on the Blood Lipid of Dietary Hyperlipemia Model in Rats Observe the effects of different doses of FTZEC on the serum TC, TG, LDL-C, and HDL-C of hyperlipemia rats.

The hyperlipemia model in rats were successfully copied according to the literature reported methods.

The animals were randomly divided: 96 rats were randomly divided into eight groups after numbering and weighting, 12 rats in each group, ① blank control group; ② hyperlipemia model group; ③ FTZ group; ④ lovastatin group; ⑤ Fenofibrate group; ⑥⑦⑧ were FTZEC high, medium and low doses experimental group in turn. In addition to ordinary feed in control group, other groups were given high fat emulsion in 10 ml/kg every morning by gavage beside the ordinary feed, and given corresponding drugs 4 hours after feeding, in which the normal group and the model groups were given equal amount of normal saline, administrated for continuous 8 weeks. These animals were fasted for 1 d, when water was given, in the next morning, the blood was taken from orbital veniplex after the last administration, centrifuged and separated the serum to test the TC, TG, HDL-C, LDL-C respectively.

2.2 Effects on the Lipid Metabolism of the Whole Hyperlipidemia New-Zealand Female Rabbit Model Purebred New Zealand female rabbits were unsexed and fed with 0.5% cholesterol diet, and intravenously injected with bovine serum albumin to establish the model. The experimental animals were 49 New Zealand Angora purebred female rabbits, 1.8-2.2 kg, 3-4 months old which were provided by Guangdong Province Experimental Animal Center. The rabbits were fed with high fat diet (the proportion of the diet included 0.5% cholesterol, 3% lard, and 96.5% base feed). After adaptive feed for 1 week, the rabbits were randomly divided into four groups: ① sham-operated control group; ② unsexed high lipid model group; ③ compound Fufang tiaozhi FTZ group; ④ lovastatin group; ⑤ fenofibrate group; ⑥ FTZEC high dose group, ⑦ FTZEC low dose group; 7 rabbits in each group. In the sham-operated group, the sham operation was confirmed (cutting a small piece of fat tissues around the ovary), without removing the ovaries. The rabbits were given ordinary commercial feed (120-150 g/d) after surgery. For the other 6 groups: in the model group and each administration group, the bilateral oophorectomy were carried out through abdomen and the rabbits were given high-fat diet after surgery (120-150 g/d) and intravenously injected with bovine serum albumin (250 mg/kg, once every 4 weeks). In the compound Fufang tiaozhi FTZ group (equal to five times of clinical adult daily dose) and other administration groups, the rabbits were administrated with drugs by gavage. The control group and the model group were fed and administrated by gavage with same volume of normal saline. The body weights were examined at 12 weeks of the experiment. 2 ml blood was taken by the ear artery for blood lipid measurement. The rabbits were fasted for 16 h before each blood sampling. The whole blood samples were placed at the room temperature for 3 h and centrifuged at 2200 r/min for 15 min, the upper serum was separate-loaded and stored at −20° C. The total cholesterol, triglyceride, HDLC and LDLC were detected by automatic biochemical analyzer and the steps were carried out according to the kit instructions. The OX-LDL in plasma was measured by ELISA, according to kit instructions.

2.3 Statistical Methods

The data was represented as x±s and the variance analysis and multiple comparisons between means were confirmed by SSP10.0 software.

3 Results
3.1 Affect on the Lipid of Dietary Hyperlipidemia Rats

The results showed that FTZEC can significantly reduce total cholesterol, triglycerides and low-density lipoprotein in serum of Dietary hyperlipidemia rats, significantly increase high-density lipoprotein, which has effects of regulating the blood lipid. The results were showed in Table 3.

TABLE 3

Affect of FTZEC on the lipid of Dietary hyperlipidemia rats

| Group | dose mg/kg | TC mmol/L | TG mmol/L | LDL-C mmol/L | HDL-C mmol/L |
|---|---|---|---|---|---|
| Normal control | 0 | 2.18 ± 0.19 | 1.02 ± 0.28 | 0.70 ± 0.09 | 1.31 ± 0.12 |
| high lipid control | 0 | 3.32 ± 0.49** | 3.28 ± 0.79** | 1.43 ± 0.30** | 0.71 ± 0.30** |
| FTZ | 5 | 2.43 ± 0.41▲▲ | 1.71 ± 0.65▲▲ | 0.95 ± 0.42▲▲ | 1.26 ± 0.41▲▲ |
| Lovastatin | 3 | 2.29 ± 0.32▲ | 2.08 ± 0.82▲ | 0.91 ± 0.25▲▲ | 0.96 ± 0.26▲▲ |
| Fenofibrate | 3 | 2.85 ± 0.45▲▲ | 1.55 ± 0.65▲▲ | 0.89 ± 0.42▲▲ | 1.22 ± 0.43▲▲ |
| FTZEC | 2 | 2.89 ± 0.43▲ | 2.31 ± 0.53 | 1.09 ± 0.45 | 1.12 ± 0.40 |
| FTZEC | 5 | 2.55 ± 0.36▲▲ | 2.05 ± 0.50▲ | 0.93 ± 0.40▲▲ | 1.21 ± 0.37▲▲ |
| FTZEC | 10 | 2.36 ± 0.37▲▲ | 1.58 ± 0.43▲▲ | 0.79 ± 0.25▲▲ | 1.29 ± 0.19▲▲ |

Note:
compared with control group, **$P < 0.01$;
compared with the STZ model group, $F = 3.82$, ▲$P < 0.05$, ▲▲$p < 0.01$.
3.2 affect on the lipid of Dietary hyperlipidemia New-Zealand female rabbits The results showed that FTZEC can significantly reduce total cholesterol, triglycerides and low-density lipoprotein in serum of Dietary hyperlipidemia unsexed New-Zealand female rabbits, significantly increase high-density lipoprotein, which has effects of regulating the blood lipid. The results were showed in Table 4.

TABLE 4

Affect of FTZEC on the lipid of Dietary hyperlipidemia New-Zealand female rabbits

| Group | Dose mg/kg | TC mmol/L | TG mmol/L | LDL-C mmol/L | HDL-C mmol/L | Ox-LDL mmol/L |
|---|---|---|---|---|---|---|
| Control group | 0 | 2.58 ± 0.19 | 1.42 ± 0.38 | 0.76 ± 0.09 | 1.51 ± 0.12 | 0.46 ± 0.09 |
| High lipid model group | 0 | 33.92 ± 3.49* | 3.98 ± 0.79* | 11.63 ± 2.30* | 0.871 ± 0.30* | 1.63 ± 0.30* |
| Pravastatin | 3 | 12.69 ± 3.62▲ | 2.08 ± 0.82▲ | 10.29 ± 2.27▲ | 1.36 ± 0.28▲ | 1.29 ± 0.27▲ |
| Fenofibrate | 3 | 19.89 ± 2.62▲ | 1.88 ± 0.82▲▲ | 4.99 ± 2.25▲▲ | 1.06 ± 0.26▲ | 0.99 ± 0.25▲▲ |
| FTZ | 10 | 12.95 ± 2.40▲ | 1.81 ± 0.48▲▲ | 4.91 ± 2.45▲▲ | 1.32 ± 0.38▲▲ | 0.91 ± 0.45▲▲ |
| FTZEC | 5 | 18.05 ± 2.43▲ | 2.01 ± 0.53▲ | 6.09 ± 2.63▲▲ | 1.22 ± 0.40▲ | 1.09 ± 0.45▲▲ |
| FTZEC | 10 | 10.76 ± 2.37▲▲ | 1.56 ± 0.43▲▲ | 4.85 ± 1.25▲▲ | 1.39 ± 0.19▲▲ | 0.88 ± 0.25▲▲ |

Note:
compared with the control group,
*$P < 0.01$; compared with the model group, $F = 3.82$,
▲$P < 0.05$,
▲▲$p < 0.01$.

FTZ and FTZEC have significant lipid-lowering effects on Dietary hyperlipidemia rats/rabbits and represented as some dose-effect relationship. FTZ and FTZEC have the functions for preventing experimental lipid metabolism disorder and the mechanism of functions may include the following:

(1) Through a series of animal studies on FTZEC, the results showed that the prescription has significant lipid-lowering efficacy, dual role of prevention and treatment of high blood lipids, multiple roles of improving hemorheology, anti-oxidation, anti-atherosclerosis in addition to affecting the key enzymes for lipid metabolism and effectively regulating the blood lipids.

(2) The results have proved that FTZEC can greatly enhance the activity of LPL and HL in hyperlipidemia model rat serum and promote the expression of HL mRNA expression in rats liver cells.

(3) Anti-oxidation, scavenging free radicals and preventing lipid peroxidation The polyphenol components contained in FTZEC has activities of scavenging free radicals, which can inhibit lipid peroxidation and reduce the formation of Ox-LDL.

(4) Function of against inflammatory factors:
Some inflammatory factors have important actions on the occurrence of atherosclerosis. The tumor necrosis factor (TNF-α) can increase the output of FFA, resulting in endothelial hyperplasia and atherosclerosis. Salvianolic acid, danshensu and flavones in FTZEC can inhibit the cell adhesion activated by ICAM-1 and TNF-α, resist the actions of the two cell factors and inhibit the vascular endothelial cells apoptosis induction by TNF-α and ICAM-1 so that against atherosclerosis.

Example 5

Clinical Validation of Prevention and Treatment of High Serum Glucose and Serum Lipid Syndrome 60 cases with hyperlipemia treated by FTZEC were analyzed, using the tablets obtained in Experiment 1.
The experiment was confirmed according to Principles for Clinical Study of New Chinese Medicines in hyperlipemia, Ministry of Health of the People's Republic of China.
1 Clinical Data
60 cases were in-patients or out-patients with hyperlipidemia diagnosed according to diagnostic criteria (1985), of which 40 cases were outpatients and 20 cases were in-patients; the patients were randomly divided into two groups, the treatment group and the control group. In the treatment group, there were 30 cases, of which 16 cases were male, 14 cases female, with age of 39 to 65 years, mean age (51.3±8.6)

years, and the disease course of hyperlipidemia was 3~15 years, with average course of 6.8±2.9 years; 19 cases were complicated with hyperlipidemia, 10 cases were complicated with coronary heart disease, and 12 cases were complicated with hypertension. In the control group, there were 30 cases, of which 15 cases were male, 15 cases female, with age of 38~65 years, mean age (51.5±6.8) years, and the disease course of hyperlipidemia was 2.5~16 years, with average course of 6.9±3.1 years; 20 cases were complicated with hyperlipidemia, 9 cases were complicated with coronary heart disease, and 10 cases were complicated with hypertension. The two groups were statistically treated in gender, age, course, complications, and there was no significant difference (P>0.05), which was comparable.

2 Diagnostic Criteria

Western diagnostic criteria (according to WHO expert consultation report in 1999):

Plasma total cholesterol (TC)≧6.0 mmol/L, and total plasma triglyceride (TG)≧0.54 mmol/L, plasma high-density lipoprotein (HDL-C)≦1.04 mmol/L.

High blood pressure was determined by reference to the staging classification of hypertension developed by World Health Organization/International Hypertension League in 1999.

The diagnostic criteria in traditional Chinese medical science refer to Principles for Clinical Study of New Chinese Medicines in hyperlipemia, Ministry of Health of the People's Republic of China. The patients with the following symptoms were the eligible experimenters: pharyngoxerosis, tireness and weakness, bulimia, thirst with desire for drinks, shortness of breath, heat sensation in chest, palmes and soles, cardiopalmus and insomnia, pain in chest and hypochondrium, red urine and constipation, red or dark red tongue, purple or petechia petechiae, petechia and ecchymosis, deep wiry pulse or taut and unsmooth pulse, qi and yin deficiency and blood stasis in collateral.

3 Treatment Methods

In the treatment group, the patients took the tablets prepared in Experiment 1, one tablet each time, twice a day. 2 months were one course, and other lipid-lowering drugs and blood pressure medicine were stopped during this time. In the control group, pravastatin sodium tablets were taken, one tablet each time, twice a day, for 2 month. All patients accepted hyperlipidemia education, diet control, and regular exercise. All patients were observed for 2 months.

4 Observation Indexes

The blood pressure and blood lipid were detected before and after treatment: total cholesterol, triglyceride, low density lipoprotein and high density lipoprotein and blood flow changes (Capillary whole blood: liver and kidney functions and urine routine were examined, and the blood pressure was detected at 2, 4, 6 weeks during the treatment).

5 Clinical Efficacies 5.1 Efficiency standard: develop refer to "Principles for Clinical Study of New Chinese Medicines in hyperlipemia" as a reference.

5.2 Efficiency standard of blood lipid Clinical control: the experimental examination returned to normal. Marked effective: the blood lipid detection achieved any one of the following indexes: TC decreased by ≧20%, TG decreased by ≧40%, and HDL-C increased by ≧0.26 mmol/L. Effective: the blood lipid detection achieved any one of the following indexes: TC decreased by ≧10% but <20%, TG decreased by ≧20% but <40%, and HDL-C increased by ≧0.104 mmol/L but <0.26 mmol/L. Invalid: the detected blood lipid did not meet the above standards. Note: when determine the efficacy of the complicated hyperlipidemia, if the two indicators were not consistent, the lower efficacy was determined as the final result.

In the two groups, the total cholesterol and triglyceride of patients were examined after fasting and 2 hours postprandial. The total cholesterol and triglyceride of patients were significantly decreased in the treatment group, and there was significant difference compared with the control group (P<0.01). In the control group, the indexes were decreased, but there was no significant difference, which suggested that FTZEC has significant efficacy in treating the hyperlipidemia. The blood lipid and changes in blood flow change before and after treatment were shown in Table 5, Table 6 and Table 7:

TABLE 5

Affect of FTZEC tablet on lipid levels in hypercholesterolemic patients

| Items | FTZEC treatment group (n = 30) Before treatment | after treatment | Pravastatin Sodium Tablets (n = 30) Before treatment | after treatment |
|---|---|---|---|---|
| TC (mmol/L) | 7.69 ± 0.62 | 3.69 ± 0.61*▲ | 7.52 ± 0.49 | 2.98 ± 0.55 |
| TG (mmol/L) | 0.72 ± 0.15 | 0.35 ± 0.13** | 0.74 ± 0.16 | 0.51 ± 0.14 |
| LDL-C (mmol/L) | 1.85 ± 0.37 | 1.31 ± 0.43** | 1.88 ± 0.41 | 1.42 ± 0.37 |
| HDL-C (mmol/L) | 0.93 ± 0.18 | 1.39 ± 0.32** | 0.95 ± 0.19 | 1.32 ± 0.33 |

TABLE 6

Statistics of efficacy of FTZEC tablet on high cholesterol

| Drugs | n | Marked effective Cases | Rate % | Effective Cases | Rate % | Invalid Cases | Rate % | Total effective rate % |
|---|---|---|---|---|---|---|---|---|
| FTZEC | 30 | 12 | 40.0 | 16 | 53.3 | 2 | 6.7 | 93.3* |
| Pravastatin | 30 | 11 | 36.7 | 15 | 50.0 | 4 | 13.3 | 86.7 |

Note:
compared with the Pravastatin group,
*P < 0.05,
**P < 0.01

The blood flow changes of patients before and after treatment were shown in Table 7. The results suggested that the composition of extracts from plants can treat high blood lipids and has significant effect on improving the hemorheology in hypercholesterolemic patients.

TABLE 7

Blood flow changes of patients before and after treatment in the treatment and control group

| Items | Treatment group (n = 30) Before treatment | after treatment | Control group (n = 30) Before treatment | after treatment |
|---|---|---|---|---|
| Blood viscosity high shear (200/s) | 6.49 ± 0.73 | 5.21 ± 0.31*▲ | 6.5 ± 0.49 | 6.03 ± 0.55 |
| | 13.40 ± 2.65 | 11.02 ± 2.13** | 13.44 ± 2.67 | 12.58 ± 2.60 |
| blood viscosity low shear (3/s) | 1.85 ± 0.37 | 1.51 ± 0.43** | 1.88 ± 0.41 | 1.72 ± 0.37 |
| | 4.29 ± 0.86 | 3.17 ± 0.62** | 4.25 ± 0.91 | 3.56 ± 0.73 |
| plasma viscosity (mpa/s) fibrinogen (g/L) | | | | |

Note:
compared with this group before treatment, **P < 0.01;
compared with the control group after treatment, ▲P < 0.05.
Conclusion: modern pharmacological studies showed that FTZEC has effects of lipid-lowering and improving lipid metabolism. For experimental hyperlipidemia, FTZEC has significant effects of lowering triglyceride and cholesterol, improving lipid metabolism, and lowering LDL-C and increasing HDL-C. FTZEC has similar effects as pravastatin and fenofibrate.

Clinical results showed that the FTZEC has significant effects of lipid-lowering and improving lipid metabolism and hemorheology, which has curative clinical effects in treatment of high blood cholesterol and lipid metabolism-related diseases Example 6

The tablets prepared from Experiment 1 were examine by HPLC, and the detection results of the active ingredients per tablet were shown in Table 8:

TABLE 8

HPLC detection results of FTZEC tablets

| Detecting item | Content (mg/tablet) | Detecting item | Content (mg/tablet) |
|---|---|---|---|
| oleanolic acid | 6.02 | panax notoginseng polysaccharides | 1.56 |
| salvianolic acid | 2.58 | finger citron polysaccharide | 2.67 |
| danshensu | 2.55 | linarin | 0.91 |
| berberine | 2.57 | kaempferol | 0.54 |
| panax notoginseng saponins | 2.50 | quercetol | 0.52 |
| aucubin | 1.50 | apigenin | 0.51 |
| polysaccharides of atracty-lodes macrocephala koidz | 2.52 | | |

The tablets prepared in Example 1 were used for clinical treatment of hyperlipidemia, twice a day, one tablet each time, for 60 days. As a result, the total cholesterol and triglyceride of the patients were decreased significantly after treatment in treatment group, and the total lipid-lowering effective rate was 93.3% and there was significant difference compared with the control group (P<0.01).

Experiment 7

3 portions of oleanolic acid, 1 portion of salvianolic acid, 1 portion of danshensu, 1 portion of berberine, 1 portion of *panax notoginseng* saponins, 2 portions of polysaccharides of atracty-lodes macrocephala koidz, 1 portion of aucubin, 2 portions of total flavone in *cirsium japonicum*, 2 portions of finger citron polysaccharide, 2 portions of *panax notoginseng* polysaccharides, and 2 portions of flavones were taken to prepare 7.2 kg of the composition of extracts from plants.

Added 10 kg of starch and 7.8 kg of dextrin into the FTZEC, mixed and loaded into No. 3 capsules to obtain 200,000 FTZEC capsules, each capsule weighed 0.125 g and contained 36 mg of FTZEC. The content results of each active ingredient determined by HPLC were shown in Table 9:

TABLE 9

HPLC detection results of FTZEC capsules

| Detecting item | Content (mg/tablet) | Detecting item | Content (mg/tablet) |
|---|---|---|---|
| oleanolic acid | 6.02 | panax notoginseng polysaccharides | 3.99 |
| salvianolic acid | 2.03 | finger citron polysaccharide | 3.96 |
| danshensu | 2.01 | linarin | 1.02 |
| berberine | 1.99 | kaempferol | 1.33 |
| panax notoginseng saponins | 1.98 | quercetol | 1.30 |
| aucubin | 1.95 | apigenin | 1.32 |
| polysaccharides of atracty-lodes macrocephala koidz | 3.93 | | |

The resulted capsules were used for clinical treatment of hyperlipidemia, twice a day, one capsule each time, for 60 days. As a result, the total cholesterol and triglyceride of the patients were decreased significantly after treatment in treatment group, and the total lipid-lowering effective rate was 90.5% and there was significant difference compared with the control group (P<0.01).

Experiment 8

4 portions of oleanolic acid, 2 portions of salvianolic acid, 1 portion of danshensu, 2 portions of berberine, 1 portion of *panax notoginseng* saponins, 1 portions of polysaccharides of atracty-lodes macrocephala koidz, 1 portion of aucubin, 1 portions of total flavone in *cirsium japonicum*, 1 portion of finger citron polysaccharide, 1 portion of *panax notoginseng* polysaccharides, and 1 portion of flavones were mixed to prepare 3.2 kg FTZEC.

The above FTZEC were added with 10 kg of starch, 2.4 kg of dextrin, and 8.0 kg of honey, prepared into water-honeyed pill and dried to obtain 20 kg dried pills, followed by packing into 100,000 pills, 0.20 g/pill (each pill contains 32 mg of FTZEC). Oral dose: 1 pill each time, 2 times a day.

The content results of actives ingredient in honeyed pills determined HPLC were shown in Table 10:

TABLE 10

HPLC detection results of FTZEC3 honeyed pills

| Detecting item | Content (mg/tablet) | Detecting item | Content (mg/tablet) |
|---|---|---|---|
| oleanolic acid | 8.02 | *panax notoginseng* polysaccharides | 1.93 |
| salvianolic acid | 4.00 | finger citron polysaccharide | 1.91 |
| danshensu | 1.98 | linarin | 0.65 |
| berberine | 3.95 | kaempferol | 0.65 |
| *panax notoginseng* saponins | 1.96 | quercetol | 0.63 |
| aucubin | 1.94 | apigenin | 0.62 |
| polysaccharides of atracty-lodes macrocephala koidz | 1.95 | | |

The resulted honeyed pills were used for clinical treatment of hyperlipidemia, twice a day, one pill each time, for 60 days. As a result, the total cholesterol and triglyceride of the patients were decreased significantly after treatment in treatment group, and there was significant difference compared with the control group (P<0.01), and the total lipid-lowering effective rate was 91.5%

The invention claimed is:

1. A composition for treating hyperlipidemia in a subject in need thereof, said composition comprising 3-10 portions by weight of oleanolic acid, 1-5 portions by weight of salvianolic acid, 1-5 portions by weight of danshensu, 1-3 portions by weight of berberine, 1-5 portions by weight of *panax notoginseng* saponins, 1-5 portions of polysaccharides of atracty-lodes macrocephala koidz, 1-3 portions by weight of aucubin, 1-5 portions by weight of total flavone in *cirsium japonicum*, 1-5 portions by weight of finger citron polysaccharide, 1-5 portions by weight of *panax notoginseng* polysaccharides, and 1-5 portions by weight of flavones, wherein the flavones are a mixture of kaempferol, quercetol and apigenin; and wherein said composition reduces total cholesterol, total triglycerides, and/or low density lipoproteins, and reduces total lipids by about 90.5% to about 93.3% when the composition is administered in an effective amount.

2. The composition of claim 1, wherein the composition is in the form of a granular formulation, tablets, capsules, powders, pills, an elixir or an oral preparation.

3. The composition of claim 1, wherein said composition increases high density lipoproteins when administered to a human in an effective amount.

4. The composition of claim 1, wherein said composition reduces HMG-CoA reductase activity by up to about 100% in a dose dependent manner, and reduces cholesterol biosynthesized by HMG-CoA synthesis.

* * * * *